(12) United States Patent
Havler et al.

(10) Patent No.: US 7,288,225 B2
(45) Date of Patent: Oct. 30, 2007

(54) IRRADIATION OF ISPAGHULA

(75) Inventors: Michael Edward Havler, Long Riston (GB); Peter William Dettmar, Patrington (GB); Glyn Owen Phillips, Cardiff (GB); Saphwan Al-Assaf, Wrexham (GB)

(73) Assignee: Reckitt Benckiser Healthcare (UK) Limited, Berkshire (GB)

( * ) Notice: Subject to any disclaimer, the term of this patent is extended or adjusted under 35 U.S.C. 154(b) by 312 days.

(21) Appl. No.: 10/258,894

(22) PCT Filed: May 10, 2001

(86) PCT No.: PCT/GB01/02040

§ 371 (c)(1),
(2), (4) Date: Mar. 25, 2003

(87) PCT Pub. No.: WO01/85190

PCT Pub. Date: Nov. 15, 2001

(65) Prior Publication Data

US 2003/0156972 A1    Aug. 21, 2003

(30) Foreign Application Priority Data

May 10, 2000    (GB)    ................... 0011169.0

(51) Int. Cl.
*A61L 2/08* (2006.01)
(52) U.S. Cl. .................. 422/22; 424/738; 426/240
(58) Field of Classification Search ............ 422/22; 424/738; 426/240
See application file for complete search history.

(56) References Cited

U.S. PATENT DOCUMENTS 3,992,147 A    11/1976  Christian et al. .............. 21/58
5,688,775 A *  11/1997  Renn et al. .................... 514/54
6,063,061 A *  5/2000   Wallace et al. ............. 604/181
2003/0027883 A1* 2/2003 Phillips et al. ................ 522/80

FOREIGN PATENT DOCUMENTS

| EP | 0105195 A2 | 4/1984 |
| EP | 0308003 A2 | 3/1989 |
| GB | 1184514    | 3/1970 |
| GB | 2145320 A  | 3/1985 |
| GB | 2310126 A  | 8/1997 |
| WO | WO 96/00094 | 1/1996 |

OTHER PUBLICATIONS

Gopal, N. G. S. et al. "Effect of Heat Ethylene Oxide and Gamma Radiation on Psyllium Husk," Indian Journal of Pharmaceutical Sciences, (1987) vol. 49, No. 2, pp. 75-76.*

Dem' Yanenko, V. H. et al. "Radiation Technology of the Preparation of Phyto Drugs," Farmatsevtychnyi Zhurnal (Kiev), (1989) No. 1, pp. 45-47.*

Lokhande, H.T.; Varadarajan, P.V. "A New Guargum-based Superabsorbent Polymer Synthesised Using Gamma Radiation as a Soil Additive," Bioresource Technology, v. 42(2), 1992, p. 119-22.*

* cited by examiner

*Primary Examiner*—E. Leigh McKane
(74) *Attorney, Agent, or Firm*—Fish & Richardson P.C.

(57) ABSTRACT

Ispaghula (material from the plant *Plantago ovata*, useful as an agent in relieving constipation, is subjected to treatment with -radiation at a dose of up to 13 kGy, and preferably in the range 5-10 kGy. As well as effecting sterilisation of the ispaghula, this dose of irradiation has been shown to offer surprising rheological advantages.

7 Claims, 2 Drawing Sheets

IRRADIATION OF ISPAGHULA

BACKGROUND OF THE INVENTION

Figure 1:
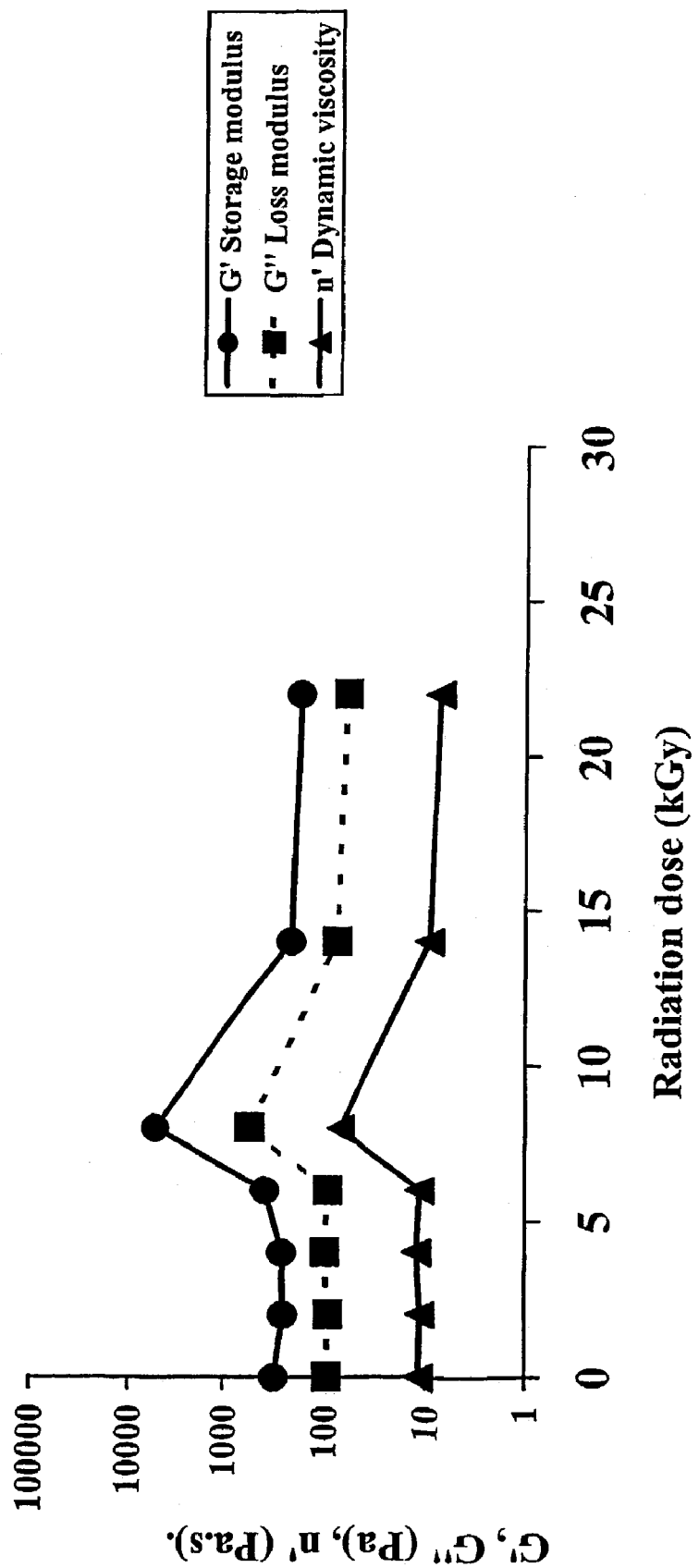

The present invention relates to a method for the production of medicinal compositions, in particular to a method for the production of ispaghula-containing compositions wherein the ispaghula is sanitised and optimised for inclusion in ingestible compositions. Ispaghula is obtained from the plant species *Plantago ovata*. Ispaghula is sometimes referred to as psyllium.

Ingestible ispaghula-containing compositions for the relief of gastric and digestive dysfunctions are known. The efficacy of ispaghula for the relief of such dysfunctions, including constipation, is well recognised and commercial formulations are readily available. Examples of such compositions include particulate ispaghula intended to be stirred in measured amount into a volume of liquid, usually water or a soft drink. After stirring, the drinking composition is intended to be quickly imbibed due to the propensity of the ispaghula to absorb water readily and swell to form a viscous gel-like mass. It is the property of water absorption which is the desired characteristic of ispaghula in compositions for gastric and digestive dysfunctions. Once the ispaghula has absorbed water to produce the gel-like mass, the mass is relatively insoluble and fibrous, and is transported through the gut quickly with minimal digestion, helping to alleviate constipation and the like.

Other forms, such as tablet forms for ingestion, are also available, such tablets being designed to be broken down in the gut, wherein the released ispaghula absorbs water from the gut to form the viscous mass.

It is usual for the ispaghula in such compositions to comprise the seed husks or hulls of the ispaghula plant. The seeds, including the husks, are usually harvested from the plant, then dried, then subjected to a mechanical treatment, to separate the seed kernels from the husks. The broken husks then generally make up over 50% by weight of the ispaghula portion of the ingestible composition, with the remaining ispaghula portion predominantly being the seed kernels themselves. In many methods the seed kernels are removed, because they are less palatable than the husks. The ispaghula can be processed, following removal of the seeds if wished, by grinding, flaking or other known operations but may be used without any further processing.

As the ispaghula used in such compositions is a natural product obtained from plants, purity is of great concern. As the ispaghula compositions are to be imbibed or otherwise consumed, it is desired that the ispaghula is sanitised to kill off any foreign biological matter such as insects and microorganisms entrapped within the ispaghula material.

Various methods have been proposed to sanitise the ispaghula, including raising the ispaghula to elevated temperatures to provide a heat sterilising effect, and contacting the ispaghula with steam to provide a stream sterilising or "autoclaving" effect. Although both forms of sanitising provide effective sterilising effects there are some associated problems, such as swelling of the ispaghula due to absorption of water during the sterilisation process. This renders the ispaghula sterilised by these processes difficult to formulate into granules, powders or tablets.

As mentioned hereinbefore, one of the most desirable characteristics of ispaghula when used in the relief of gastric and digestive dysfunctions is its ability to absorb water in the gut and form a viscous, fibrous mass which is quickly transported through the gut without absorption from it.

Thus from the foregoing it is apparent that there is a need for the provision of a process for treating ispaghula which renders the ispaghula safe for human consumption whilst not introducing absorbed water to the ispaghula during the process, the process also maintaining or improving the capability of the ispaghula to absorb water in the gut after ingestion.

It is therefore an object of preferred embodiments of the present invention to overcome or mitigate the shortcomings of the known processes described above.

SUMMARY OF THE INVENTION

It has now been determined that a process involving subjecting the ispaghula to a dose of radiation, preferably ionising radiation, within a confined dose range, renders the ispaghula safe for human consumption without introducing water by absorption during the process. Furthermore the process appears to effect unexpected improvements in the water absorption characteristics of the ispaghula.

Therefore, according to the present invention there is provided a method for the production of an ingestible composition comprising ispaghula, the method comprising the step of irradiating the ispaghula, such that the dose of radiation absorbed by the ispaghula is at least 4 kGy and no more than 13 kGy.

DETAILED DISCLOSURE

The dose of radiation absorbed by the ispaghula is suitably sufficient to effect sanitisation. Suitably is at least 5 kGy, preferably at least 6 kGy, and more preferably at least 7 kGy. Preferably it does not exceed 12 kGy, and most preferably does not exceed 10 kGy. 1 kGy (Gray) equals 1 Joule per kilogram.

Although we are not bound by any theory, it is believed that in its untreated form (that is, without irradiation) the ispaghula has a fairly compact tertiary structure of long polysaccharide chains, able to absorb a certain amount of water in a reasonably short period of time in the gut. The absorption of water in the gut swells the ispaghula to form a fairly viscous gel-like mass which is not readily absorbed by the gut and travels quickly through it.

It is believed that irradiation of the ispaghula with a dose defined above causes breakages in certain of the long chain polysaccharides present in the ispaghula. It is believed that this opens up the fairly compact tertiary structure in a specific manner to form a more ordered and viscous structure. It is thought that the ispaghula therefore forms an even more viscous gel-like mass in the gut providing more effective alleviation of symptoms of gastric and digestive dysfunctions.

In certain embodiments of the invention the dose of radiation absorbed by the ispaghula is less than 7 kGy. In such embodiments we believe, without being bound by any theory, that the dose of radiation again breaks down certain of the long chain polysaccharides present in ispaghula into smaller-chain polysaccharides. However with the smaller dose of radiation it is believed that the polysaccharides do not break down to the extent required to open up the tertiary structure of the ispaghula but form internal traps which allow specific interaction with water. Ingestion of the treated ispaghula allows colonic bacteria to continue the degradation required to further open up the tertiary structure and allow increased water absorption to swell the ispaghula to the optimum viscosity for quick passage through the gut.

Any suitable type and source of radiation may be used which confers the desired properties on the ispaghula upon irradiation at a dose within the range defined above. The radiation used during the method may be corpuscular (for example α-particles or β-particles) or, preferably, electromagnetic (for example x-rays or, more preferably, γ-rays). Preferably the radiation used during the method is γ-radiation. The frequency of the γ-radiation is typically in the range $10^{20}$-$10^{24}$ Hz. The source of the preferred γ-radiation may suitably be a Cobalt-60 source or, preferably a Caesium-137 source.

The ispaghula used in the method of the invention may comprise whole ispaghula seeds, but preferably at least part of the ispaghula comprises separated ispaghula seed husks. More preferably the ispaghula comprises at least 50% wt separated ispaghula husks, most preferably at least 95% wt separated ispaghula husks. Suitably the remainder of the ispaghula comprises other seed parts and/or other ispaghula plant materials. In preferred compositions the seeds kernels themselves have been substantially removed to leave the husks.

The ispaghula may undergo mechanical processing, for example granulation or flaking, and this may occur prior to irradiation or after irradiation.

Preferably the ispaghula is mixed with one or more co-ingredients to form the desired ingestible composition.

It is noted that in the method of the present invention the ispaghula is irradiated prior to mixing with the co-ingredients but it can be envisaged that in certain embodiments of the invention the co-ingredients are mixed with the ispaghula before irradiation, the amount of radiation being absorbed by the ispaghula component of the formulation being kept at no more than 13 kGy by suitable adjustment of the dose rate.

Suitable co-ingredients may, for example, be selected from one or more of bicarbonates, for example sodium bicarbonate, ingestible acids, for example citric acid, flavourings and colourings.

The invention also extends to a composition comprising ispaghula when provided by the irradiation method described herein.

The composition may be formed into a solid tablet or capsule for direct ingestion by a user. Preferably the composition is provided in a particulate solid form, for example as powder or flakes intended to be mixed with water, immediately prior to ingestion by a user.

The invention will now be described by way of example with reference to FIGS. 1 and 2 which are plots showing the relevant properties of ispaghula treated in accordance with the invention.

EXAMPLE 1

Ispaghula husk material (1 kg) obtained from *Plantago ovata*, and broken down to enable the seed kernels to be removed, was taken at random from a 25 kg sack. Samples of the ispaghula material (4 g) were placed in glass stoppered tubes and introduced to a radiation source ($^{137}$Cs, γ-source) for varying time periods to achieve a range of treatment dose levels. The dose rate of the source was determined using a Fricke dosimeter found to be 0.65 kGy/min. From this accurately determined rate, the dose to each sample could be calculated respectively as 2 kGy, 4 kGy, 6 kGy, 8 kGy, 15 kGy and 22 kGy, It was determined by gel permeation chromatography (GPC) and multi-angle laser light scattering (MALLS) (carried out on the polysaccharide extracted from the ispaghula material suspended in water/0.1 M sodium hydroxide overnight) that there was a reduction in molecular weight of the polysaccharide extracted from the irradiated ispaghula material, the effect becoming more pronounced as the radiation dose increased.

To determine the effect of this molecular weight reduction on the physical behaviour of the ispaghula material, a Theological analysis of the whole ispaghula husk (not just the extractable polysaccharide) was undertaken.

Samples (0.2 g) of irradiated ispaghula husk material, from which seed kernels had been removed and control samples (0.2 g) of corresponding non-irradiated material were allowed to hydrate for 2 days in 5 ml aliquots of physiological saline (0.15 M sodium chloride). At the end of the hydration period, the samples were stirred gently to mix any separated layers, before being applied to a Carrimed CS 150 controlled stress rheometer (T.A. Instruments Ltd., U.K.) fitted with a cone and plate geometry to determine the viscoelastic behaviour. Storage (G') and loss (G") moduli were monitored at over a frequency sweep of 0.1-10 Hz, along with dynamic viscosity of the ispaghula.

Storage modulus (G') is the elastic storage of energy and is a measure of how well structured a material is. Large values of G' are obtained when the material is predominantly elastic or highly structured. If the structure is building up within a sample, G' will increase. On the other hand, if the structure is being destroyed, G' will decrease. G' can also be called the elastic or rigidity modulus.

Loss modulus (G") represents viscous dissipation or loss of energy and is related to the dynamic viscosity. If G" is large then the sample is predominantly a viscous liquid. Dynamic viscosity is a measure of the viscosity of the sample under investigation and is related to G" by the following equation $$n'=G''/\omega$$

where ω is the angular frequency (ω=2π×frequency (Hz)).

The results of this Example 1 are shown in FIG. 1. This graph presents storage modulus (G'), loss modulus (G") and dynamic viscosity (n'), at a frequency of 1.29 Hz plotted as a function of irradiation dose for the 4 wt % ispaghula husk in 0.15 M sodium chloride.

The results of this Example 1 show that when the ispaghula husks are subjected to doses of absorbed radiation up to about 7 kGy the storage modulus loss modulus and dynamic viscosity are largely unaffected. It is believed to be the case that the long-chain polysaccharides in the ispaghula husks are beginning to be broken down to smaller-chain polysaccharides, but not enough to affect the compact, relatively structured tertiary structure of the ispaghula. Thus as no further ordering of the structure is occurring there is little opening up of the structure or increase in viscosity over non-irradiated samples.

When the ispaghula husks are subjected to doses of absorbed radiation of around 7 kGy the storage and loss moduli and the dynamic viscosity can be seen to increase, compared with non-irradiated samples. The increase is a very substantial one, given that the y-axis uses a logarithmic scale. This change is believed to be due to the long-chain polysaccharides in the ispaghula husks being broken down to smaller-chain polysaccharides and internal traps sufficient to open up the compact tertiary structure of the ispaghula. Once the structure is opened up it becomes more ordered during interaction with water and the viscosity increases.

It is thought possible that when the ispaghula is subjected to doses of radiation below about 7 kGy, the partial breakdown of the polysaccharide occurs and the centers so produced can continue to breakdown in the body, by the action of colonic bacteria, to structures similar to those produced by subjecting the ispaghula to higher doses of radiation.

EXAMPLE 2

This was a larger scale example. A series of 200 g samples, all taken from a single 25 kg sample, were subjected to γ-irradiation in plastic bags, using a $^{60}$Co source. One sample was irradiated at 6 kGy, one at 8 kGy, one at 10 kGy and one at 13 kGy. A control sample was unirradiated. 4 wt % suspensions were allowed to hydrate for 24 hours before their storage modulus, loss modulus and dynamic viscosity were measured as described above, also at a frequency of 1.29 Hz.

Figure 2:
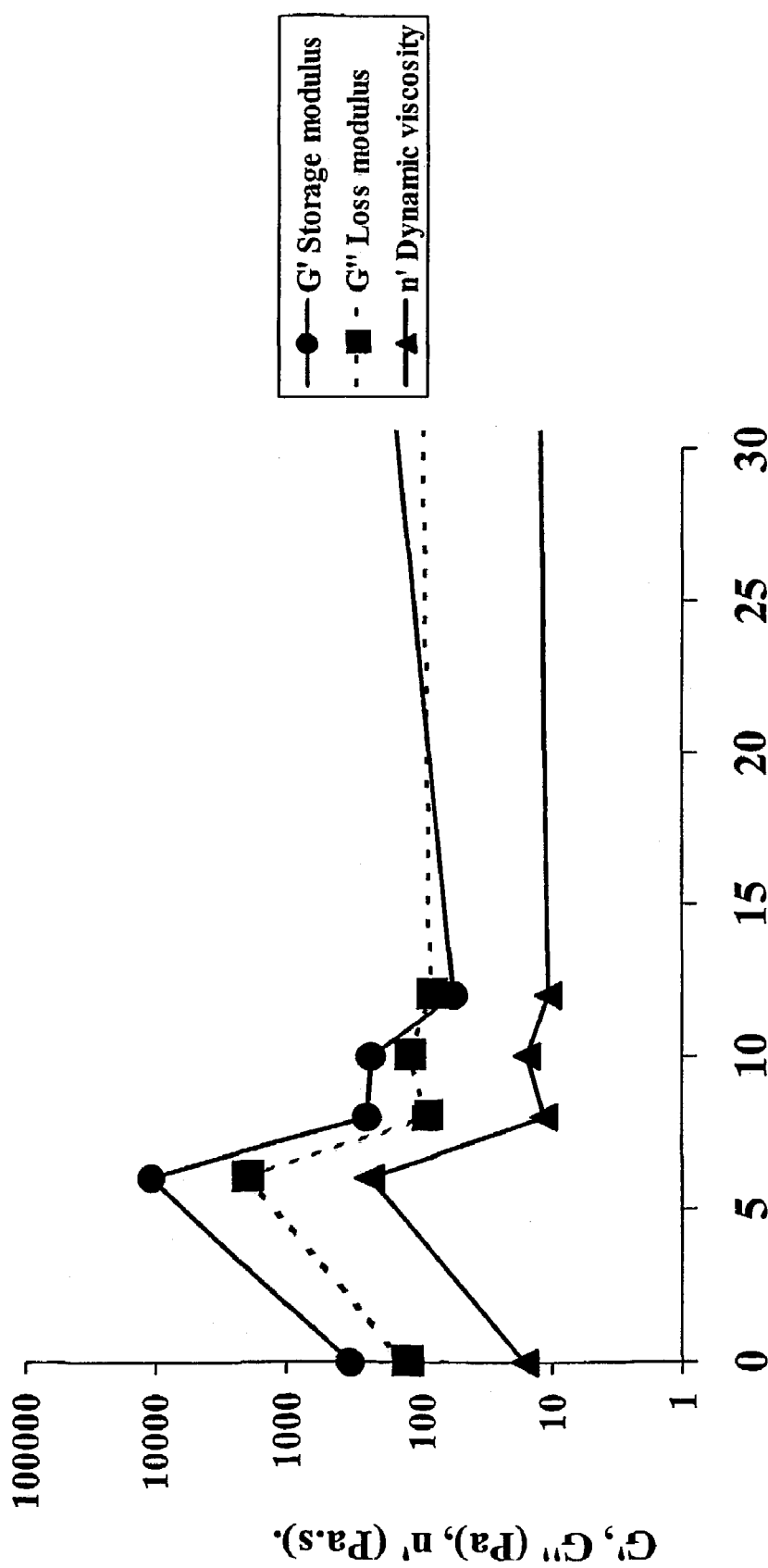

The results are shown in FIG. 2. It will be seen that the plots are similar to those shown in FIG. 1, except that the peak improvement is seen with a radiation dose of 6 kGy, rather than 8 kGy. This may be a function of the batch of ispaghula used, of the orientation of the chains in the ispaghula, of the larger scale employed, of the γ-source used or of the tolerances involved in the test, particularly as regards the measurement of irradiation in the larger scale method. In any event however, the experiments of Examples 1 and 2 are consistent in showing substantial specific beneficial effects centred around the 6-8 kGy mark.

The invention claimed is:

1. Ispaghula which has been treated by irradiation such that the radiation absorbed by the ispaghula is from about 6 kGy to about 8 kGy, wherein the ispaghula comprises at least 95 wt. % of separated ispaghula husks and substantially no ispaghula seed kernels.

2. An ingestible composition comprising ispaghula as claimed in claim 1 together with one or more co-ingredients which enhance palatability.

3. A composition as claimed in claim 2, in the form of a particulate solid intended to be mixed with water prior to ingestion.

4. A composition as claimed in claim 2, in the form of a tablet or capsule intended to be swallowed or chewed by a patient.

5. A method of increasing the water absorption capability of an ingestible composition comprising ispaghula, which method comprises the steps of (1) providing ispaghula husk material from which substantially all seed kernels have been removed and (2) irradiating the said ispaghula husk material such that the dose of radiation absorbed ranges from about 6 kGy to about 8 kGy.

6. The method as claimed in claim 5 wherein the ispaghula husk material comprises at least 95 wt. % separated ispaghula husks and substantially no ispaghula seed kernels.

7. The method as claimed in claim 5 in which the radiation is γ-radiation.

* * * * *